(12) United States Patent
Shen et al.

(10) Patent No.: US 9,029,762 B2
(45) Date of Patent: May 12, 2015

(54) DOWNHOLE SPECTROSCOPIC DETECTION OF CARBON DIOXIDE AND HYDROGEN SULFIDE

(75) Inventors: Jing Shen, Houston, TX (US); Christopher M Jones, Houston, TX (US); Michael T Pelletier, Houston, TX (US); Robert Atkinson, Richmond, TX (US); Mark Proett, Missouri City, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 213 days.

(21) Appl. No.: 13/520,558

(22) PCT Filed: May 21, 2010

(86) PCT No.: PCT/US2010/035695
§ 371 (c)(1),
(2), (4) Date: Jul. 4, 2012

(87) PCT Pub. No.: WO2011/146068
PCT Pub. Date: Nov. 24, 2011

(65) Prior Publication Data
US 2013/0056626 A1    Mar. 7, 2013

(51) Int. Cl.
*G01V 5/08* (2006.01)
*E21B 49/08* (2006.01)
*E21B 47/10* (2012.01)
(Continued)

(52) U.S. Cl.
CPC ............... *E21B 49/081* (2013.01); *E21B 47/10* (2013.01); *G01N 21/33* (2013.01); *G01N 21/3504* (2013.01); *G01N 21/3581* (2013.01); *G01N 21/359* (2013.01); *G01N 21/65* (2013.01); *G01N 2021/3595* (2013.01);
(Continued)

(58) Field of Classification Search
CPC ..................... G01N 21/3504; G01N 33/2841
USPC ........................................... 250/269.1–269.8
See application file for complete search history.

(56) References Cited

U.S. PATENT DOCUMENTS

| 5,859,430 A | 1/1999 | Mullins et al. |
| 6,218,662 B1 | 4/2001 | Tchakarov et al. |

(Continued)

FOREIGN PATENT DOCUMENTS

| CN | 101375141 A | 2/2009 |
| CN | 101375143 A | 2/2009 |

(Continued)

OTHER PUBLICATIONS

IP Australia, Patent Examination Report No. 1, AU Patent Application No. 2010353761, which is the counterpart AU application to the instant application, May 23, 2014.

(Continued)

*Primary Examiner* — Kiho Kim
(74) *Attorney, Agent, or Firm* — Howard L. Speight, PLLC

(57) ABSTRACT

The present invention relates to a method for measuring the characteristics of a downhole fluid. The method for measuring the characteristics of a downhole fluid includes passing a downhole fluid sample through an analyzer, analyzing the downhole fluid sample by illuminating the downhole fluid sample with light from a light source and detecting light that interacts with the fluid sample. The method is applicable to detecting carbon dioxide and/or hydrogen sulfide directly in a downhole environment.

27 Claims, 9 Drawing Sheets

(51) Int. Cl.
  *G01N 21/3504* (2014.01)
  *G01N 21/33* (2006.01)
  *G01N 21/3581* (2014.01)
  *G01N 21/359* (2014.01)
  *G01N 21/65* (2006.01)
  *G01N 21/35* (2014.01)
  *G01N 21/39* (2006.01)

(52) U.S. Cl.
  CPC ... *G01N 2021/399* (2013.01); *G01N 2021/653* (2013.01); *G01N 2201/129* (2013.01)

(56) References Cited

U.S. PATENT DOCUMENTS

| | | | |
|---|---|---|---|
| 6,274,865 | B1 | 8/2001 | Schroer et al. |
| 6,292,756 | B1 * | 9/2001 | Lievois et al. ............ 702/50 |
| 6,437,326 | B1 | 8/2002 | Yamate et al. |
| 6,627,873 | B2 | 9/2003 | Tchakarov et al. |
| 6,662,116 | B2 | 12/2003 | Brown |
| 6,678,050 | B2 | 1/2004 | Pope et al. |
| 6,825,657 | B2 * | 11/2004 | Kleinberg et al. ......... 324/303 |
| 6,995,360 | B2 | 2/2006 | Jones et al. |
| 7,240,546 | B2 | 7/2007 | DiFoggio |
| 7,336,356 | B2 | 2/2008 | Vannuffelen et al. |
| 7,379,180 | B2 | 5/2008 | Vannuffelen et al. |
| 7,516,654 | B2 | 4/2009 | DiFoggio |
| 2002/0074489 | A1 | 6/2002 | Mullins et al. |
| 2002/0121370 | A1 | 9/2002 | Kurkjian et al. |
| 2003/0134426 | A1 | 7/2003 | Jiang et al. |
| 2003/0223068 | A1 | 12/2003 | DiFoggio |
| 2005/0029125 | A1 | 2/2005 | Jiang et al. |
| 2005/0269499 | A1 | 12/2005 | Jones et al. |
| 2006/0032301 | A1 | 2/2006 | DiFoggio |
| 2006/0139646 | A1 | 6/2006 | DiFoggio |
| 2006/0243603 | A1 | 11/2006 | Jiang et al. |
| 2008/0023328 | A1 | 1/2008 | Jiang et al. |
| 2008/0245960 | A1 | 10/2008 | Csutak |
| 2008/0257730 | A1 | 10/2008 | Jiang et al. |
| 2009/0107667 | A1 | 4/2009 | Mullins et al. |
| 2009/0166085 | A1 | 7/2009 | Ciglenec et al. |
| 2009/0235731 | A1 | 9/2009 | Zuo et al. |

FOREIGN PATENT DOCUMENTS

| | | |
|---|---|---|
| CN | 1423745 | 6/2013 |
| GB | 2344365 | 7/2000 |
| GB | 2409902 | 4/2006 |
| WO | 02066964 A2 | 8/2002 |
| WO | 02084334 A1 | 10/2002 |

OTHER PUBLICATIONS

Canadian Intellectual Property Office, Examiner's Letter in CA Application No. 2,786,581, which is the counterpart Canadian application to the instant application, mailed on Jun. 13, 2014.
Canadian Intellectual Property Office, Examiner's Letter in CA Application No. 2786581 which is the counterpart Canadian application to the instant application, mailed on Nov. 28, 2013.
International Searching Authority, International Preliminary Report on Patentability in PCT/US2010/035695, which is the PCT parent of the instant matter, mailed Jul. 23, 2010.
The State Intellectual Property Office of the People'S Republic of China, Notice on the First Office Action, Application/Patent No: 201080064837.2, which is a counterpart to the instant application, Jan. 12, 2015.
The State Intellectual Property Office of the People'S Republic of China, Translation of Notice on the First Office Action, Application/Patent No: 201080064837.2, which is a counterpart of the instant application, Jan. 12, 2015.
Canadian Intellectual Property Office, Examiners Letter in CA Application No. 2,786,581, which is the counterpart Canadian application to the instant application, mailed on Jan. 13, 2015.

* cited by examiner

DOWNHOLE SPECTROSCOPIC DETECTION OF CARBON DIOXIDE AND HYDROGEN SULFIDE

FIELD OF THE INVENTION

The present invention generally relates to the analysis of downhole fluids in a geological formation. More particularly, the present invention relates to apparatus and methods for analyzing carbon dioxide and/or hydrogen sulfide concentration downhole in a borehole.

BACKGROUND OF THE INVENTION

Hydrocarbon producing wells may contain many different formation liquids and gases such as methane, ethane, and other higher hydrocarbons, as well as carbon dioxide, hydrogen sulfide, water, and other compounds. In order to evaluate the commercial value of a hydrocarbon producing well, or as an aid in operations and well planning, it is often useful to obtain information by analyzing the component concentrations of the produced fluid from a formation or an individual well. Numerous systems have been developed to evaluate a downhole fluid composition and the relative component concentrations in the downhole fluid.

It has been found that certain components in downhole fluids can lead to corrosion. Among the problems encountered with well tubulars, corrosion may be the factor that causes the most losses. In general, there are four types of corrosion: sweet, sour, oxygen, and electrochemical. Sour corrosion is found in oil and gas wells that contain $H_2S$ (hydrogen sulfide) gas. $H_2S$ also presents health risks that need to be addressed and planned for. Wells may also produce other undesirable corrosive components such as $CO_2$. A good understanding of the downhole fluid and gas concentrations is desirable in an attempt to control corrosion rates and to plan for safe development and production of the hydrocarbons.

Wellbore monitoring typically involves determining certain downhole parameters in producing wellbores at various locations in one or more producing wellbores in a field, typically over extended time periods. Spectroscopy is a known technique for analyzing downhole fluids, including drilling muds and crude oil. For instance, methods are known for analyzing drilling muds that involve reflectance or transmittance infrared (IR) spectroscopy. Spectroscopy is typically emitted in wellbore environments in the near infrared-range of from 1000 to 2500 nm. Spectroscopy is typically emitted in this range because near IR emitters and sensors are known to be easier to operate at well temperatures while longer wavelength emitters have shown limited output optical power under similar well conditions.

Typically, spectroscopy monitoring involves obtaining a formation fluid sample downhole and bringing the sample to the surface where measurements and processing of the resultant data takes place. These measurement methods are typically utilized at relatively large time intervals and thus do not provide continuous information about wellbore condition or that of the surrounding formations.

Methods for analyzing downhole fluids can include the use of wireline tools. Methods of measuring using wireline tools include lowering a wireline tool including an analyzer into a wellbore at a desired depth. These wireline tools may contain spectroscopic imaging tools for detecting the contents of downhole fluids. An alternate method can include the use of tubing for conveying the tools downhole. The tubing can be conventional jointed tubing or could be coiled tubing or any other suitable types of tubular pipe. The tubing can be wired, such as having signal conveyance wires connected or adjacent to the tubing for providing a means of transmitting signals to the surface.

Other methods for analyzing downhole fluids can include the method of logging while drilling (LWD) or measurement while drilling (MWD). LWD and MWD are techniques of conveying well logging tools or measurement tools into the wellbore as part of a bottomhole assembly. During drilling of the wellbore, these downhole tools are disposed in a bottomhole assembly above the drill bit. In some methods, LWD/MWD tools contain spectroscopic imaging tools for detecting the contents of downhole fluids.

In a current $H_2S$ detection method, $H_2S$ is detected by spectroscopy using an indirect method wherein metal ions are mixed with $H_2S$, thereby forming metal sulfide. The metal sulfide is then subjected to near-range spectroscopy to detect the amount of metal sulfide present downhole. The amount of metal sulfide detected by spectroscopy can be used to indicate the amount of hydrogen sulfide present downhole. The metal sulfide produced from this method, however, may contaminate the oil in the wellbore.

In a current $CO_2$ detection method, a sample is decompressed to enable gaseous components to come out of solution from the sample. The gaseous components are then analyzed and $CO_2$ is detected by spectroscopy. The content of the $CO_2$ in the sample is then determined by the results of the liquid and gaseous analysis. Therefore the $CO_2$ in the sample is determined indirectly.

Therefore, there is a need to directly detect $H_2S$ and/or $CO_2$ in a downhole environment without causing further contamination and without the separation of gaseous components from the sample being analyzed. In particular, it can be desirable to detect $H_2S$ and/or $CO_2$ in a wellbore without stopping production. In addition, it can be desirable to obtain a continuous reading of $H_2S$ and/or $CO_2$ in a wellbore during production. Thus, a need exists for a method of directly detecting both $H_2S$ and $CO_2$ downhole.

DETAILED DESCRIPTION

The present invention relates generally to wellbore operations. More particularly, the present invention is applicable to both borehole investigative logging and to production logging. The present invention includes downhole tools such as wireline tools and logging while drilling (LWD) or measurement while drilling (MWD) tools, well formation testing tools, drill-stem testing, as well as any other tool capable of being used in a downhole environment.

In wireline measurements, a downhole tool, or logging tool, can be lowered into an open wellbore on a wireline. Once lowered to the bottom of the depth of interest, the measurements can be taken at various depths or continually as the tool is pulled out of the wellbore. LWD/MWD tools take measurements in much the same way as wireline-logging tools, except that the measurements are typically taken by a self-contained tool near the bottom of the bottomhole assembly and can be recorded during or in conjunction with drilling operations. An alternate method can include the use of tubing for conveying the tools downhole. The tubing can be conventional jointed tubing or could be coiled tubing or any other suitable types of tubular pipe. The tubing can be wired, such as having signal conveyance wires connected or adjacent to the tubing for providing a means of transmitting signals to the surface.

Figure 1:
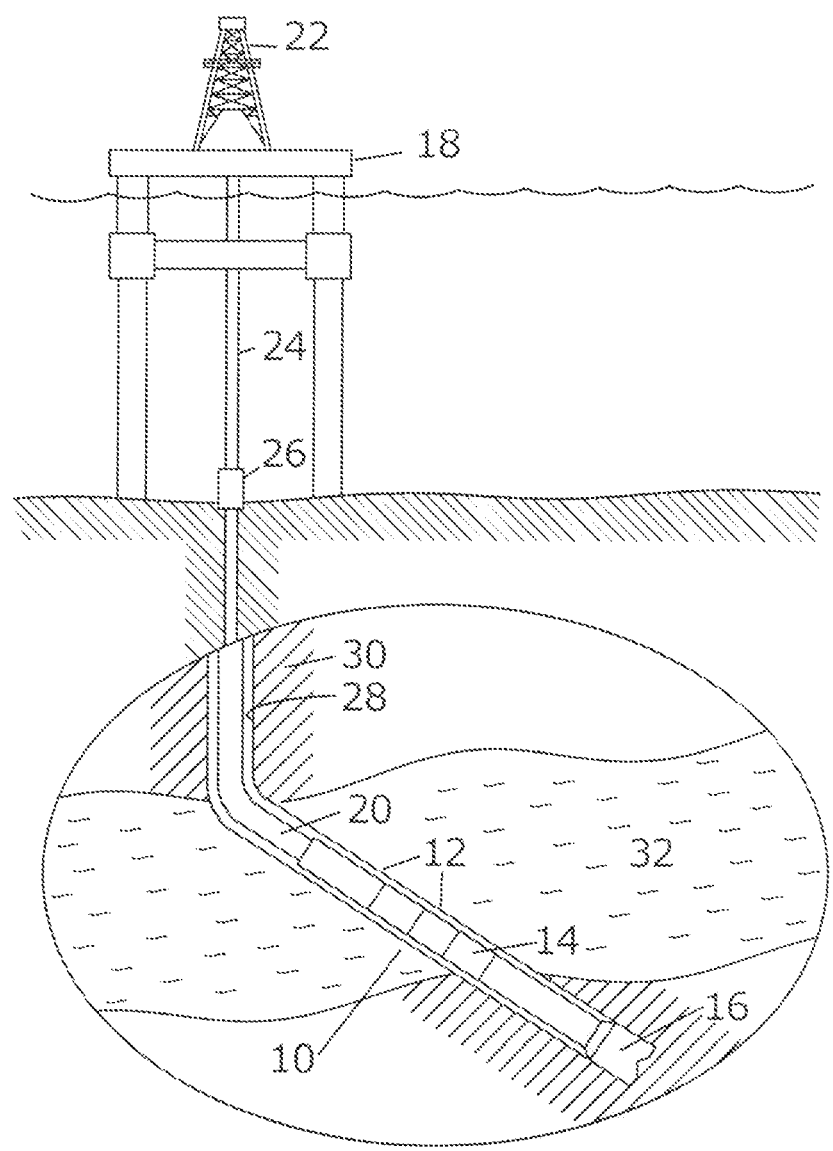
FIG. 1 illustrates a partial schematic and partial cross sectional side view of a wellbore containing a downhole tool of the invention.

FIG. 1 schematically depicts an embodiment of a downhole tool, here described as a formation fluid identification tool 10, as part of a bottomhole assembly 12, which includes a sub 14 and a drill bit 16 positioned at the distal most end of the formation fluid identification tool 10. During operation, as shown, the bottomhole assembly 12 is lowered from a drilling platform 18, such as a drill ship or other conventional platform, via a drill string 20. The drill string 20 is disposed through a riser 24 and a wellhead 26. Conventional drilling equipment (not shown) can be supported within a derrick 22 and can rotate the drill string 20 and the drill bit 16, causing the bit 16 to form a borehole 28 through the formation material 30. The drilled borehole 28 penetrates subterranean zones or reservoirs, such as reservoir 32. According to embodiments of the present invention, the formation fluid identification tool 10 may be employed in other bottom hole assemblies and with other drilling apparatus in land-based drilling, as well as offshore drilling such as the embodiment depicted in FIG. 1. In addition to the formation fluid identification tool 10, the bottom hole assembly 12 may contain various conventional apparatus and systems, such as a downhole drill motor, a rotary steerable tool, a mud pulse telemetry system, LWD/MWD sensors and systems, drill-stem test (DST) apparatus and others known in the art.

In another embodiment, the formation fluid identification tool 10 and other components described herein may be conveyed down borehole 28 via wireline technology or on coiled tubing or any other suitable means.

Figure 2:
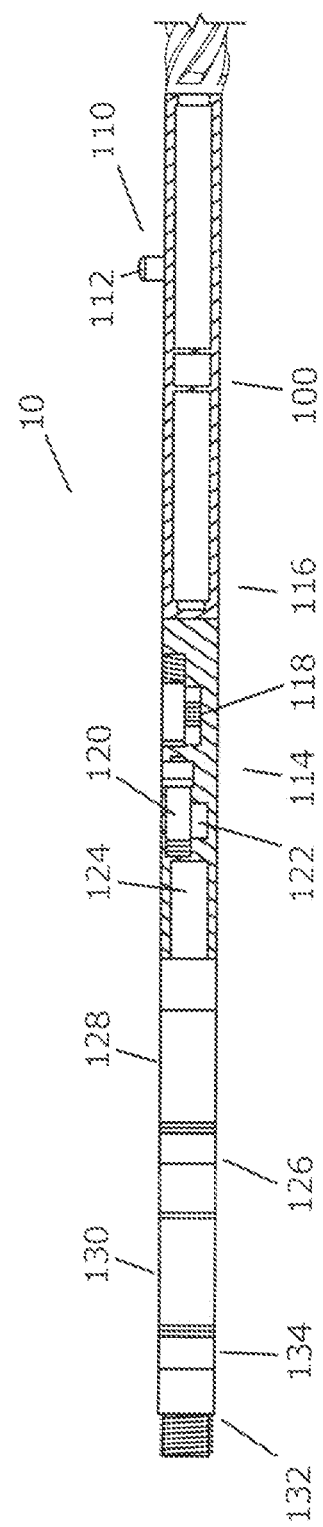
FIG. 2 depicts a partial schematic and partial cross-sectional view of one embodiment of a downhole analysis tool.

Referring to FIG. 2, an embodiment of the formation fluid identification tool 10 is shown. A first end of the tool 10 includes a drill collar section 100, also referred to as the probe drill collar section 100. For reference purposes, the first end of the tool 10 at the probe collar section 100 is generally the lowermost end of the tool, which is closest to the distal end of the borehole. The probe collar section 100 may include a formation tester or formation probe assembly 110 having an extendable sample device or extendable probe 112. The tool 10 includes a second drill collar section 114, also referred to as the power drill collar section 114, coupled to the probe collar section 100 via an interconnect assembly 116. The interconnect assembly 116 includes fluid and power/electrical pass-through capabilities such that the various connections in the interconnect assembly are able to communicate, various fluids, electrical power, and/or signals to and from the probe collar 100 and the power collar 114.

In an embodiment, the power collar 114 may include the components of a flush pump assembly 118, a flow gear or turbine assembly 120, an electronics module 122 and a drilling fluid flow bore diverter 124. A third drill collar section 126, also referred to as the sample bottle drill collar section 126, may be attached to the power collar 114. The sample bottle collar 126 may include one or more sample bottle assemblies 128, 130. A fourth drill collar section 132, also referred to as the terminator drill collar section 132, may be attached to the sample bottle collar 126. The coupling between the sample bottle collar 126 and the terminator collar 132 may include an embodiment of an interconnect assembly 134. In an alternative embodiment, the terminator collar 132 and the interconnect assembly 134 couple directly to the power collar 114 if a sample bottle collar 126 is not needed. In an embodiment the formation fluid identification tool 10 can be used in conjunction with drilling, well formation testing or drill-stem testing operations.

Figure 3:
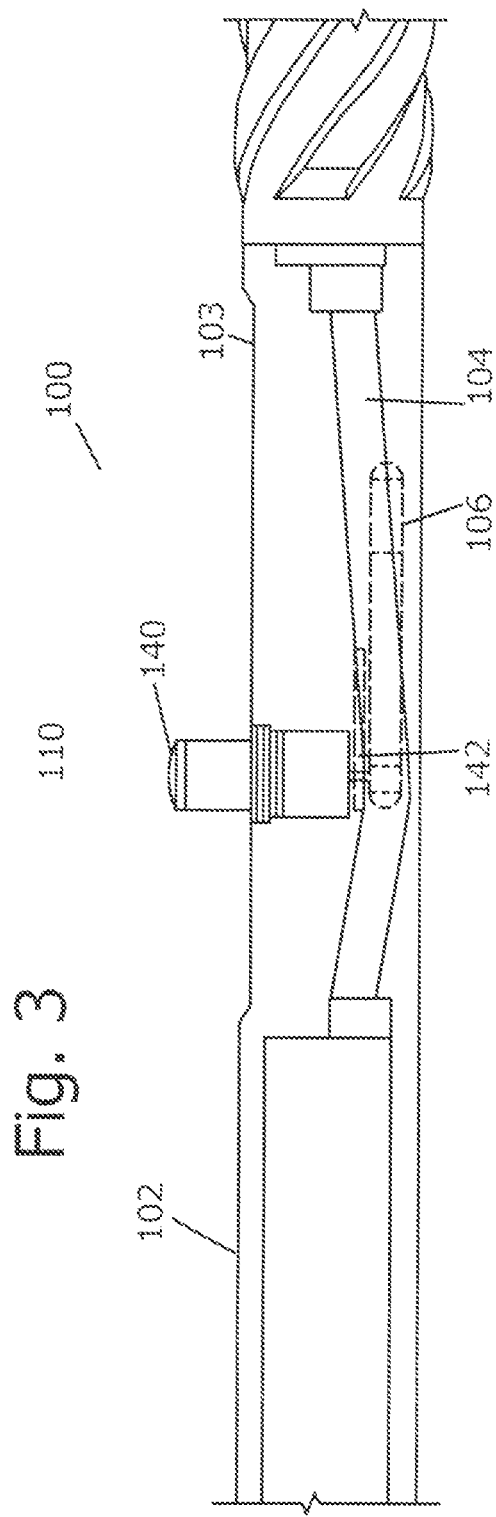
FIG. 3 depicts a partial schematic and partial cross-sectional view of one embodiment of a probe drill collar section of a downhole analysis tool.
Figure 4:
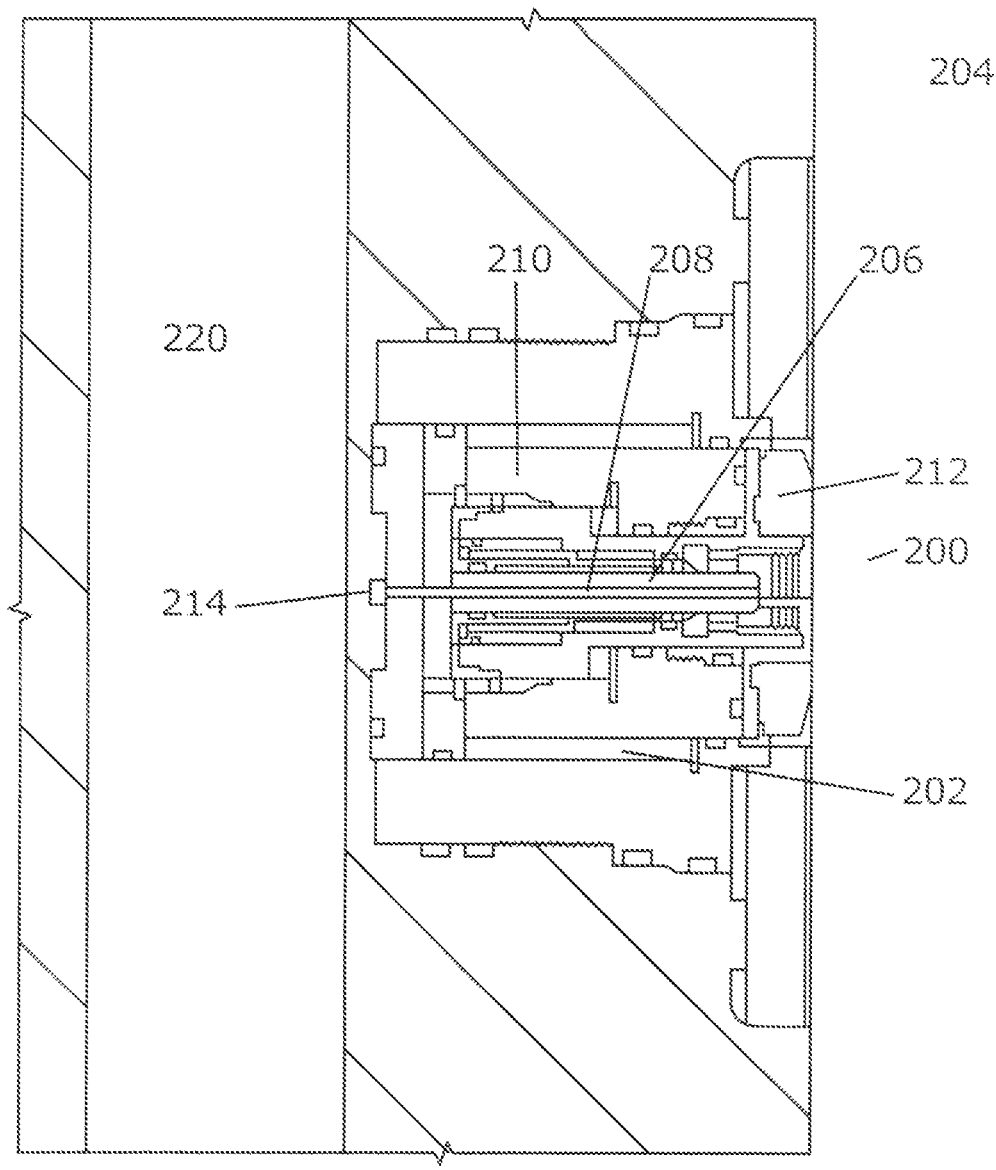
FIG. 4 is a cross-sectional view of one embodiment of a downhole analysis probe.

Referring next to FIG. 3, an embodiment of the probe collar section 100 is shown in more detail. A drill collar 102 houses the formation tester or probe assembly 110. The probe assembly 110 includes various components for operation of the probe assembly 110 to receive and analyze formation fluids. The probe member 140 is disposed in an aperture 142 in the drill collar 102 and is extendable beyond the drill collar 102 outer surfaces, as shown. The probe member 140 is retractable to a position that is flush with or recessed beneath the drill collar 102 outer surfaces, as shown in FIG. 4. The probe assembly 110 may include a recessed outer portion 103 of the drill collar 102 outer surface that is adjacent the probe member 140. The probe assembly may include a sensor 106 for receiving formation fluid from the probe member 140. The formation fluid is communicated from the probe member 140 to the sensor 106 via a flowline (not depicted) for measurement of the formation fluid. Also shown is a drilling fluid flow bore 104 through which drilling fluid can pass.

In an embodiment, the downhole tool 10 contains a probe collar section 100 that includes a flowline, which can be a tube or the like, that is isolated from the wellbore environment. The function of the downhole tool 10 is to retrieve a formation fluid sample by pulling formation fluid from the formation using the probe member 140 of the probe collar section 100. The formation fluid sample retrieved by the probe member 140 is sent through the flowline to a sample analyzer, or sensor 106, situated within the downhole tool 10. The downhole tool 10 also contains an outlet flowline (not depicted), which is used to remove the tested sample from the downhole tool 10 to the wellbore environment. The downhole tool 10 may also include pump(s) (not depicted) for moving the formation fluid sample throughout the downhole tool.

In referring to FIG. 4, an alternative embodiment is shown as probe 200. The probe 200 is retained in an opening 202 in drill collar 204. Any alternative means for retaining the probe 200 are consistent with the teachings herein, as understood by one having ordinary skill in the art. The probe 200 is shown in a retracted position, not extending beyond the outer surface of the drill collar 204. The probe 200 may include a stem 206 having a passageway 208, and a piston 210. The end of the piston 210 may be equipped with a seal pad 212. The passageway 208 communicates with a port 214, which communicates with the flowline (not shown) for receiving and carrying a formation fluid to the sample analyzer, or sensor (not shown). Also shown is a drilling fluid flow bore 220 that enables the flow of drilling fluid through the drill collar 204 without contact with the probe assembly 200.

Figure 5:
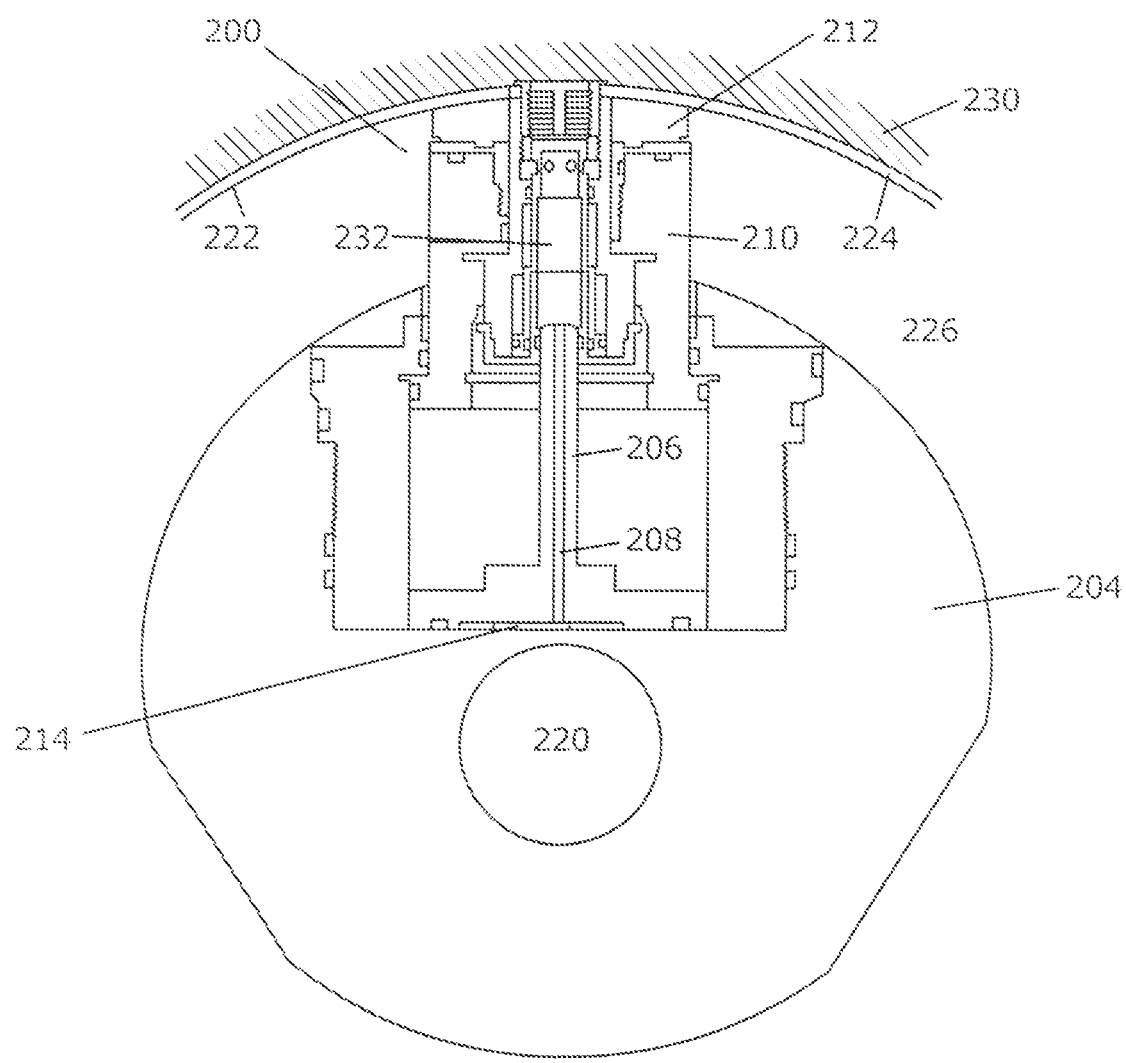
FIG. 5 depicts an alternative cross-section view of the probe of FIG. 4 in an extended position.

In reference to FIG. 5, the probe 200 is shown in an extended position. The piston 210 is actuated from a first position shown in FIG. 4 to a second position shown in FIG. 5. The seal pad 212 is engaged with the borehole wall surface 222, which may include a mud or filter cake 224, to form a primary seal between the probe 200 and the borehole annulus 226. The probe 200 may be actuated to withdraw formation fluids from the formation 230, into a bore 232, into the passageway 208 of the stem 206 and into the port 214. Also shown is a drilling fluid flow bore 220 that enables the flow of drilling fluid through the drill collar 204 without contact with the probe assembly 200.

The seal pad 212 is can be made of an elastomeric material. The elastomeric seal pad 212 seals and resists drilling fluid or other borehole contaminants of the borehole annulus 226 from entering the probe 200 during formation testing.

In an embodiment, the downhole tools of the present invention, including the wireline, tubing conveyed and LWD/MWD tools, contain a sample analyzer for analyzing a sample of formation fluid. The downhole tools may also contain a pump and flow lines for retrieving a formation fluid sample from the formation, sending the sample to the sample analyzer and removing the sample from the downhole tool after it has been analyzed. The sample analyzer may include an optical analyzer, such as a spectrometer. In an embodiment the spectrometer includes a light source and a detector. The light source and detector may be selected from all available spectroscopy technologies.

In an embodiment, any available spectroscopy method can be used in the present invention. In an embodiment, the spectroscopy is selected from the group of absorption spectroscopy, fluorescence spectroscopy, X-ray spectroscopy, plasma emission spectroscopy, spark or arc (emission) spectroscopy, visible absorption spectroscopy, ultraviolet (UV) spectroscopy, infrared (IR) spectroscopy, near-infrared (NIR) spectroscopy, Raman spectroscopy, coherent anti-Stokes Raman spectroscopy (CARS), nuclear magnetic resonance, photoemission, Mossbauer spectroscopy, acoustic spectroscopy, laser spectroscopy, Fourier transform spectroscopy, and Fourier transform infrared spectroscopy (FTIR) and combinations thereof. In another embodiment, the spectroscopy is selected from the group of infrared (IR) spectroscopy, near-infrared (NIR) spectroscopy, Fourier transform spectroscopy, and Fourier transform infrared spectroscopy (FTIR) and combinations thereof. In a specific embodiment, the spectroscopy is selected from infrared (IR) spectroscopy.

In an embodiment the light source may be selected from the group of a tunable source, a broadband source (BBS), a fiber amplified stimulated emission (ASE) source, black body radiation, enhanced black body radiation, a laser, infrared, supercontinuum radiation, frequency combined radiation, fluorescence, phosphorescence, and terahertz radiation. A broadband light source is a source containing the full spectrum of wavelengths to be measured. In an embodiment, the light source can include any type of infrared source.

In an embodiment, the light source is an infrared (IR) light source. In an embodiment, the IR light source discharges light in the mid range, also known as mid-infrared light (MIR). In an embodiment, the mid-infrared light is greater than 1900 nm. In an embodiment, the mid-infrared light is in a range of from 2000 to 5000 nm. In another embodiment, the mid-infrared light is in the range of from 2200 to 4500 nm. In an alternative embodiment, the mid-infrared light is in the range of from 4000 to 5000 nm. In an embodiment, the IR wavelengths emitted from the light source are of a sufficient wavelength to detect $H_2S$ or $CO_2$. In an alternative embodiment the light source emits mid-range IR wavelengths sufficient to detect both $H_2S$ and $CO_2$. In another embodiment the chosen IR wavelengths are sufficient to detect both $H_2S$ and $CO_2$. In a further embodiment the light source emits near-range IR wavelengths in order to detect $H_2S$ and mid-range IR wavelengths in order to detect $CO_2$. In another embodiment, the IR light source discharges light in the near-infrared (NIR) range and the mid-infrared (MIR) range.

In an embodiment the light source is directed to a fluid sample in order to detect $H_2S$ and/or $CO_2$. In an embodiment, the light source transmits light rays in a range of from 4000 to 5000 nm, which is a range for absorbance of carbon dioxide. Using Beer's Law and assuming a fixed path length, the amount of carbon dioxide in the fluid sample is proportional to the absorption of light in this range. In another embodiment, the light source transmits light rays in a range of from 1900 to 4200 nm, which is a range for absorbance of hydrogen sulfide. Data collected from these two frequency ranges may provide information for determining the amount of carbon dioxide and hydrogen sulfide in a sample.

Figure 6:
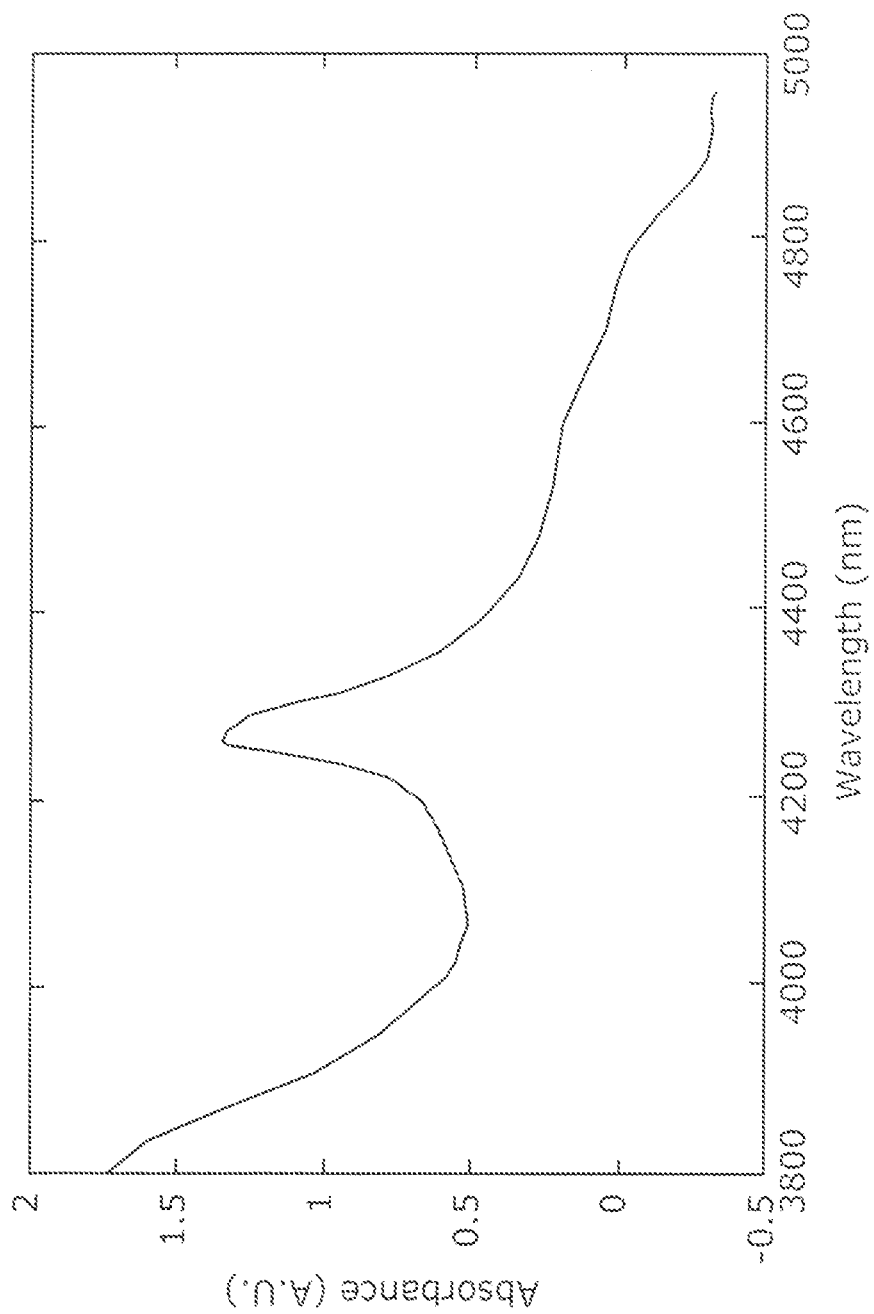
FIG. 6 is a graph of $CO_2$ spectral response between the band of 3800 and 5000 nm.

In an embodiment, the IR light source is a MIR range light source. In an embodiment the MIR range light source is a tunable light source. The tunable light source may be selected from the group of an optical parametric oscillator (OPO) pumped by a pulsed laser, a tunable laser diode, and a broadband source (BBS) with a tunable filter. In an embodiment, the tunable MIR light source is adapted to cause pulses of light to be emitted at or near a $CO_2$ absorption peak at 4300 nm. FIG. 6 is a graph of $CO_2$ spectral response between the bands of 3800 to 5000 nm that shows a carbon dioxide peak at 4300 nm. The tunable MIR source that is adapted to cause pulses of light to be emitted at or near a $CO_2$ absorption peak at 4300 nm.

Figure 7:
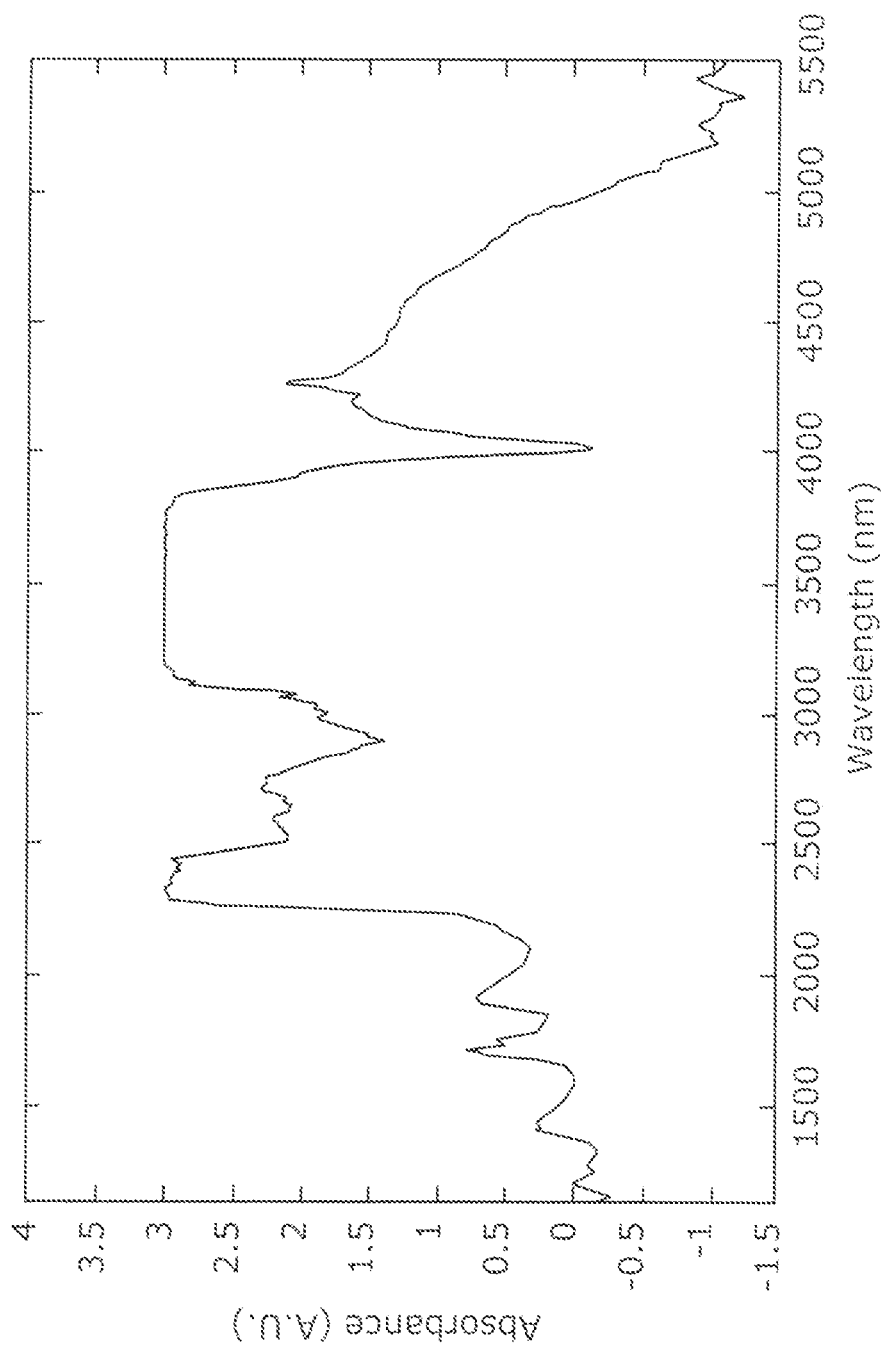
FIG. 7 is a graph of $H_2S$ spectral response between the band of 1000 and 5500 nm.

The tunable MIR source may also be combined with a tunable near-infrared (NIR) source such that the combined light source is adapted to cause pulses of light to be emitted at or near at least one $H_2S$ peak at 1900, 2300, 2600, 3800, and 4100 nm. FIG. 7 is a graph of $H_2S$ spectral response between the bands of 1500 to 5500 nm and showing $H_2S$ peaks at 1900, 2600, and 4100 nm. The plateaus at the 2300 and 3800 nm bands are in the oil absorbance region and therefore a saturated reading is obtained. The $H_2S$ peak of 4100 nm in a pure $H_2S$ sample is shifted in FIG. 7 to a peak of approximately 4300 nm due to the effect of having water in the system. The presence of $H_2O$ in the fluid sample can alter the spectral response and may need to be taken into account when analyzing a sample for $CO_2$ or $H_2S$.

Figure 8:
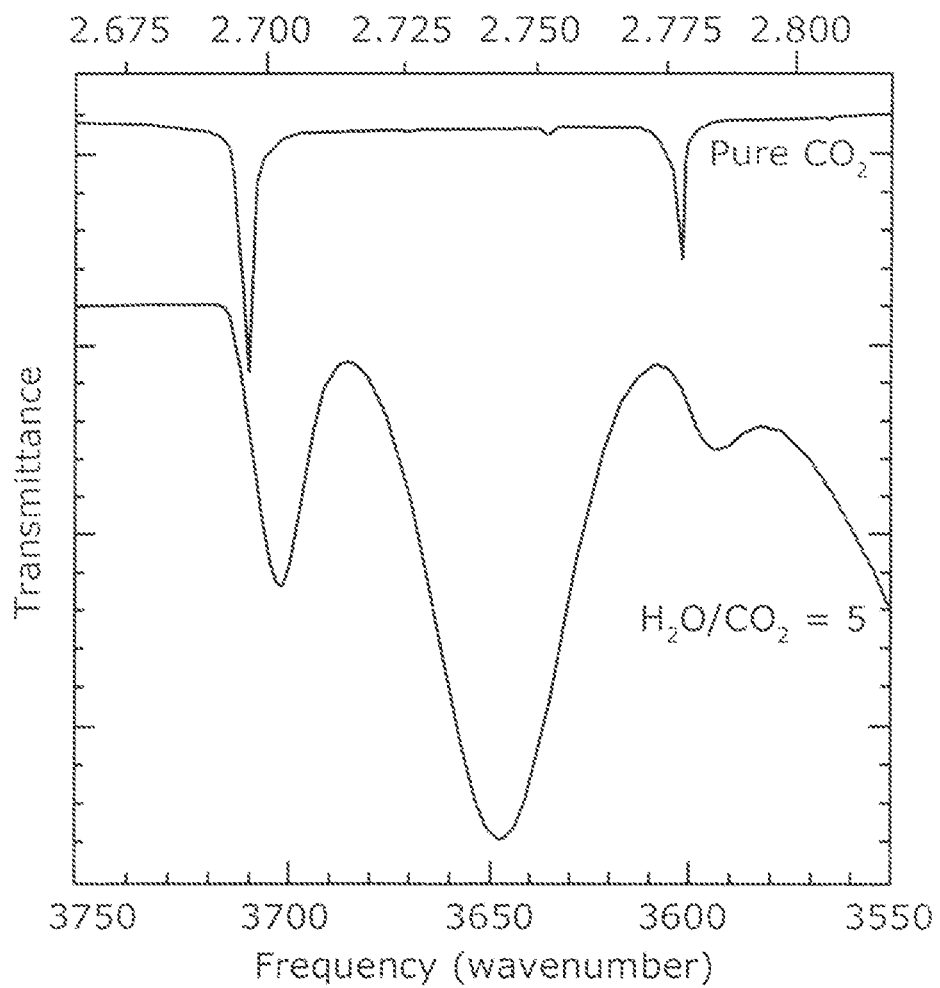
FIG. 8 is a graph of $CO_2$ spectral response illustrating the shift effect of water.
Figure 9:
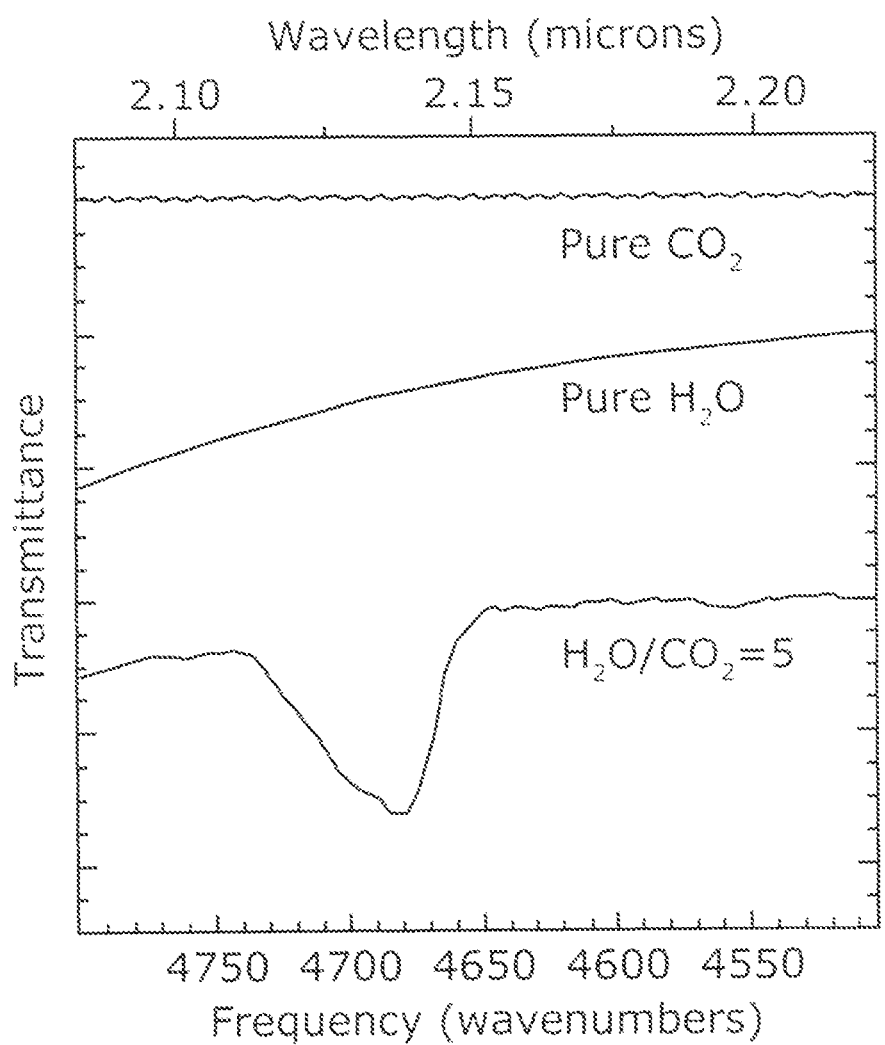
FIG. 9 is a graph illustrating a spectral effect of a mixture of water and $CO_2$.

The water content of the sample can be determined in any manner and can be determined by optical or non-optical means. The effect of $H_2O$ in the fluid sample is illustrated in FIG. 8 where a pure $CO_2$ optical response is compared to the response of a sample having a $H_2O/CO_2$ ratio of 5. The pure $CO_2$ spectral responses at 2.695 and 2.777 microns (3710 and 3601 $cm^{-1}$) are shifted to longer wavelength and are broader in shape in the sample containing water. The effect of $H_2O$ in the fluid sample is further illustrated in FIG. 9 where a pure $CO_2$ optical response and pure $H_2O$ optical response are compared to a response of a sample having a $H_2O/CO_2$ ratio of 5. Although there was no optical response in the pure $CO_2$ and pure $H_2O$ samples, the mixed sample does have a spectral response. By knowing the amount of and effect of $H_2O$ within the sample the optical response of the sample can be used to determine the $CO_2$ and $H_2O$ content of the sample. The present invention can include the determination of $H_2O$ content in the sample and the compensation, if any, of the optical response shifts for the determination of $CO_2$ and/or $H_2S$ content of the sample.

In an embodiment in which the tunable light source is a broadband source, sample detection may be improved by applying frequency modulation to the broadband source signal by modulating the drive current or by chopping so that unwanted signals can be avoided in the detector of the spectrometer by using phase sensitive detection. In another embodiment, the broadband source may be pulsed with or without frequency modulation.

In an embodiment the light source can include a laser diode array. In a laser diode array light source system, desired wavelengths are generated by individual laser diodes. The output from the laser diode sources may be controlled in order to provide signals that are arranged together or in a multiplexed fashion. In an embodiment having a laser diode array light source, time and/or frequency division multiplexing may be accomplished at the spectrometer. In an embodiment, a one-shot measurement or an equivalent measurement may be accomplished with the laser diode array. In an embodiment, either a probe-type or sample-type optical cell system may be utilized.

In an embodiment, the spectrometer includes detectors, which act as sensors detecting the light emitted from the light source after a light passes through a sample. The effectiveness of the detectors of the spectrometer may be dependent upon temperature conditions. As temperatures increase, the detectors can become less sensitive. The detectors of the present invention may include an improvement in detector technology. In an embodiment, the detectors of the present invention may have reduced thermal noise and can have an increased sensitivity to the emitted light. In an embodiment, the detector is selected from the group of thermal piles, photoacoustic detectors, thermoelectric detectors, quantum dot detectors, momentum gate detectors, frequency combined detectors, high temperature solid gate detectors, and detectors enhanced by meta materials such as infinite index of refraction, and combinations thereof.

In an embodiment, the spectroscopy of the present invention includes conventional IR spectroscopy. In conventional IR spectroscopy, the light source can also include a splitter. In such an embodiment the light that is emitted from the light source is split into two separate beams in which one beam passes through a sample and the other beam passes through a reference sample. Both beams are subsequently directed to a splitter before passing to the detector. The splitter quickly alternates which of the two beams enters the detector. The two signals are then compared in order to detect the composition of the sample.

In an embodiment, the spectroscopy may be performed by a diffraction grating or optical filter, which allows selection of different narrow-band wavelengths from a white light or broadband source. In an embodiment, a method of utilizing a broadband source is in conjunction with Fiber Bragg Grating (FBG). FBG includes a narrow band reflection mirror whose wavelength can be controlled by the FBG fabrication process. In an embodiment the broadband light source is utilized in a fiber optic system. In an embodiment, the fiber optic system contains a fiber having a plurality of FBGs. In such an embodiment, the broadband source is effectively converted into a plurality of discrete sources having desired wavelengths.

In an embodiment, the spectroscopy of the present invention includes Fourier spectroscopy. Fourier spectroscopy, or Fourier transform spectroscopy, is a method of measurement for collecting spectra. In Fourier transform spectroscopy, rather than passing a monochromatic beam of light through a sample as in conventional IR spectroscopy, a beam containing multiple different frequencies of light is passed through a sample. This spectroscopy method then measures how much of the beam is absorbed by the sample. Next, the beam is modified to contain a different combination of frequencies, giving a second data point. This process is repeated many times. After the beams of light have been passed through the sample, the resultant data is sent to a computer, which can infer from the data what the absorption is at each wavelength. In an embodiment, the beam described above is generated by a broadband light source. The light emitted from the broadband light source shines into a designated configuration of mirrors, also known as an interferometer, that allows some wavelengths to pass through but blocks others, due to wave interference. The beam is modified for each new data point by moving one of the mirrors; this changes the set of wavelengths that pass through. As mentioned above, computer processing is used to turn the raw data, which includes the light absorption for each mirror position into the desired result, which includes light adsorption for each wavelength. This processing is also known as "Fourier transform" and the raw data is referred to as the "interferogram." When Fourier spectroscopy is utilized, a scanning process is needed to create the interferogram. That is, the spectrometer internally generates a fixed and variable length path for the optical beam and then recombines these beams, thereby generating optical interference. The resulting signal includes summed interference pattern for all frequencies not absorbed by the sample. As a result, the measurement system is not a one-shot type system, and hence the sampler-type probe is preferred for use with this type of spectrometer. In an embodiment, the Fourier spectroscopy is performed utilizing any known light source.

In an embodiment, the spectroscopy of the present invention is a Fourier spectroscopy utilizing an IR light source, also referred to as Fourier transform infrared (FTIR) spectroscopy. In an embodiment, IR light is guided through an interferometer, the IR light then passes through a sample, and a measured signal is then obtained, called the interferogram. In an embodiment Fourier transform is performed on this signal data, which results in a spectrum identical to that from conventional infrared spectroscopy. The benefits of FTIR include a faster measurement of a single spectrum. The measurement is faster for the FTIR because the information at all frequencies is detected simultaneously. This allows multiple samples to be collected and averaged together resulting in an improvement in sensitivity.

The present invention includes a method for measuring the characteristics of a downhole fluid. The method for measuring the characteristics of a downhole fluid includes the steps of pumping a downhole fluid sample through an analyzer, analyzing the downhole fluid sample by illuminating the downhole fluid sample with light from a light source and detecting light interaction to produce a range of data points that can be interpreted and that can give the content of components of the fluid sample. In an embodiment, the step of analyzing the downhole fluid sample is conducted downhole. In an embodiment, the method for measuring the characteristics of a downhole fluid is continuous. In another embodiment, the light emitted from the light source is of a sufficient wavelength to detect $CO_2$ and/or $H_2S$. In a further embodiment, the light emitted from the light source is IR light in the mid-range, or MIR. In an embodiment, the downhole fluid sample includes formation fluid. In an alternative embodiment the downhole fluid sample includes 95% or greater of formation fluid. In a more specific embodiment the downhole fluid sample is formation fluid. In a further embodiment the formation fluid sample is obtained from a formation, sent to the analyzer, subjected to analysis by illumination with a MIR light source, and then discharged to the wellbore downhole. In an embodiment, the downhole fluid sample is not removed from the downhole environment during the method of measuring. In an embodiment, the downhole fluid sample is not decompressed during the method of measuring. In an embodiment, the downhole fluid sample is not separated by components during the method of measuring.

The present invention also includes a method of detecting $CO_2$ in a downhole environment. The method of detecting $CO_2$ in a downhole environment includes the steps of pumping a downhole fluid sample through an analyzer, analyzing the downhole fluid sample by interacting the downhole fluid sample with light from a light source of sufficient wavelength to detect $CO_2$ and detecting the light interaction to produce a range of data points that can be interpreted and that can give the $CO_2$ content. In an embodiment, the $CO_2$ is detected directly from the sample. The term detected directly means that the $CO_2$ content can be calculated from the data obtained from the light interaction and does not rely on a comparison against a reference sample. In an embodiment, the method of directly detecting $CO_2$ in a downhole fluid is continuous. In a further embodiment, the light emitted from the light source is IR light in the mid-range, or MIR. In a specific embodiment, the $CO_2$ is detected by IR light having a wavelength of from 4000 to 4500 nm. In a more specific embodiment, the $CO_2$ is detected by IR light having a wavelength at 4300 nm. In an embodiment, $CO_2$ is detected by observing a peak at 4300 nm from the range of data points produced. In an embodiment, the downhole fluid sample is not decompressed during the method of measuring. In an embodiment, the downhole fluid sample is not separated by components during the method of measuring.

The present invention also includes a method of detecting $H_2S$ in a downhole environment. The method of detecting $H_2S$ in a downhole environment includes the steps of pumping a downhole fluid sample through an analyzer, analyzing the downhole fluid sample by interacting the downhole fluid sample with light from a light source of sufficient wavelength to detect $H_2S$ and detecting the light interaction to produce a range of data points that can be interpreted and that can give the $H_2S$ content. In an embodiment, the $H_2S$ is detected directly from the sample. The term detected directly means that the $H_2S$ content can be calculated from the data obtained from the light interaction and does not rely on a comparison against a reference sample. In an embodiment, the method of directly detecting $H_2S$ in a downhole fluid is continuous. In a further embodiment, the light emitted from the light source includes IR light in the mid-range, or MIR, and/or light in the near-range, or NIR. In a specific embodiment, the $H_2S$ is detected by IR light having a wavelength of from 1000 to 5000 nm. In a specific embodiment, the $H_2S$ is detected by IR light having a wavelength of from 4000 to 4500 nm. In a more specific embodiment, the $H_2S$ is detected by IR light having a wavelength selected from the group of 1900, 2600, 3800, and 4100 nm. In an embodiment, the downhole fluid sample is not decompressed during the method of measuring. In an embodiment, the downhole fluid sample is not separated by components during the method of measuring. The method can further include the determination of water content within the sample and compensating for any spectral shift due to its presence.

The present invention also includes a method of detecting $CO_2$ and $H_2S$ in a downhole environment. The method of detecting $CO_2$ and $H_2S$ in a downhole environment includes the steps of pumping a downhole fluid sample through an analyzer, analyzing the downhole fluid sample by illuminating the downhole fluid sample with light from a light source of sufficient wavelength to detect $CO_2$ and $H_2S$ and detecting light passing through the downhole fluid sample, and measuring the detected light to produce range of data points. In an embodiment, the $CO_2$ is detected directly from the sample. In an embodiment, the method of detecting $CO_2$ in a downhole fluid is continuous. In a further embodiment, the light emitted from the light source is IR light in the mid-range, or MIR. In a specific embodiment, the $CO_2$ and $H_2S$ are detected by IR light having a wavelength of from 4000 to 4500 nm. In a more specific embodiment, the $CO_2$ is detected by IR light having a wavelength at 4300 nm and $H_2S$ is detected by IR light having a wavelength at 4100 nm. In an embodiment, $CO_2$ is detected by observing a peak at 4300 nm and $H_2S$ is detected by observing a peak at a wavelength selected from the group of 1900, 2600, 3800, and 4100 nm from the range of data points produced. The method can further include the determination of water content within the sample and compensating for any spectral shift due to its presence.

The present invention also includes a downhole tool capable of detecting $CO_2$ and $H_2S$ directly in a downhole environment. The downhole tool includes a pump, an analyzer, and a probe, wherein the probe obtains formation fluid from a formation, the pump pulls formation fluid from the probe through the analyzer and out of the downhole tool, keeping the formation fluid in the downhole environment. The analyzer contains a spectrometer containing a light source and a detector. In an embodiment, the light source is an IR light source. In an embodiment, the IR light source emits IR light in the mid-infrared, MIR, range. In an embodiment, the downhole fluid sample is not decompressed during the method of measuring. In an embodiment, the downhole fluid sample is not separated by components during the method of measuring.

By measuring the amount of light detected by the detector, the amount of carbon dioxide and/or hydrogen sulfide in the formation fluid sample can be determined. This data, which was measured by spectroscopy, is sent to a processor. The processor can be operated to determine the carbon dioxide and hydrogen sulfide concentration of the fluid through the application of processing techniques. In an embodiment, the processing techniques include any known computational method. In another embodiment, the processing techniques can be selected from the group of least squares analysis, partial least squares regression (PLS), multivariate optical element (MOE), principal component analysis (PCA), principal component regression (PCR), multiple linear regression (MLR), classical least squares (CLS), analysis of variance (ANOVA), varimax rotation, singular value decomposition (SVD), multivariant curve resolution (MCR), Eigenvector Projection, chemometric methods, and mixture analysis and combinations thereof.

The term "detected directly" means that the component content can be calculated from the data obtained from the light interaction and does not rely on a comparison against a reference sample.

The term "logging" refers to a continuous measurement of formation properties with electrically powered instruments to infer properties and make decisions about drilling and production operations. The record of the measurements, typically a long strip of paper, is called a log.

The term "spectroscopy", or "spectrometry," is a spectroscopic method used to evaluate the concentration or amount of a given chemical species in a sample.

The term "spectrometer" refers to the instrument that performs spectroscopy.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee.

The invention claimed is:

1. A method of detecting carbon dioxide in a downhole environment, comprising:
    placing a downhole tool into a wellbore;
    providing a downhole fluid sample into the downhole tool;
    analyzing the downhole fluid sample in the downhole tool by illuminating the downhole fluid sample by light emitting from a light source of sufficient wavelength to detect carbon dioxide;
    detecting light that interacts with the downhole fluid sample;
    measuring the detected light to produce a range of data points that indicate the amount of carbon dioxide present in the downhole fluid sample; and
    determining an $H_2O$ content in the downhole fluid sample and compensating for any wavelength shift in the detected light and resulting data points effected by the $H_2O$ content;
    wherein the light source emits light at wavelengths of 2100 nm or greater.

2. The method of claim 1, wherein the light source is an infrared light source producing infrared light.

3. The method of claim 1, wherein the infrared light comprises wavelengths in the mid-infrared range.

4. The method of claim 3, wherein the infrared light comprises wavelengths of from 2500 to 5000 nm.

5. The method of claim 4, wherein the infrared light comprises wavelengths of from 4000 to 5000 nm.

6. The method of claim 1, wherein carbon dioxide is detected in the downhole fluid sample by observing a peak at between about 4250 nm and about 4300 nm from the range of data points produced.

7. The method of claim 1, wherein analyzing the downhole fluid sample is performed by infrared spectroscopy.

8. The method of claim 1, wherein detecting the light that passes through the downhole fluid sample further comprises using a detector selected from the group consisting of thermal piles, photoacoustic detectors, thermoelectric detectors, quantum dot detectors, momentum gate detectors, frequency combined detectors, high temperature solid gate detectors, and detectors enhanced by meta materials such as infinite index of refraction and combinations thereof.

9. A method of detecting hydrogen sulfide in a downhole environment, comprising:
    placing a downhole tool into a wellbore;
    providing a downhole fluid sample into the downhole tool;
    analyzing the downhole fluid sample in the downhole tool by illuminating the downhole fluid sample by light emitting from a light source of sufficient wavelength to detect hydrogen sulfide;
    detecting light that interacts with the downhole fluid sample;
    measuring the detected light to produce a range of data points that indicate the amount of hydrogen sulfide present in the downhole fluid sample; and
    determining any $H_2O$ content in the downhole fluid sample and compensating for any wavelength shift in the detected light and resulting data points effected by the $H_2O$ content.

10. The method of claim 9, wherein the light source is an infrared light source producing infrared light.

11. The method of claim 10, wherein the infrared light comprises wavelengths in the mid-infrared range.

12. The method of claim 10, wherein the infrared light comprises wavelengths of from 1900 to 5000 nm.

13. The method of claim 10, wherein the infrared light comprises wavelengths of from 4000 to 5000 nm.

14. The method of claim 10, wherein the infrared light comprises wavelengths in the mid-infrared range and the near-infrared range.

15. The method of claim 9, wherein the hydrogen sulfide is detected in the sample by observing peaks at one or more ranges of data points produced selected from the group comprising about 1900, about 2600 and about 4100 nm.

16. The method of claim 9, wherein analyzing the downhole fluid sample is performed by infrared spectroscopy.

17. A method of detecting carbon dioxide and hydrogen sulfide in a downhole environment, comprising:
    placing a downhole tool into a wellbore;
    providing a downhole fluid sample into the downhole tool;
    analyzing the downhole fluid sample in the downhole tool by illuminating the downhole fluid sample by light emitting from an infrared light source of sufficient wavelengths to detect carbon dioxide and hydrogen sulfide;
    detecting light that interacts with the downhole fluid sample; and
    measuring the detected light to produce a range of data points that indicate the amount of carbon dioxide and hydrogen sulfide present in the downhole fluid sample; and
    determining an $H_2O$ content in the downhole fluid sample and compensating for any wavelength shift in the detected light and resulting data points effected by the $H_2O$ content;
    wherein the infrared light source produces infrared light having wavelengths of 1900 nm or greater.

18. The method of claim 17, wherein the infrared light comprises wavelengths of from 2500 to 5000 nm.

19. The method of claim 17, wherein the infrared light comprises wavelengths of from 4000 to 4500 nm.

20. The method of claim 17, wherein the hydrogen sulfide is detected in the downhole fluid sample by observing a peak at 2300 nm from the range of data points produced and the carbon dioxide is detected in the downhole fluid sample by observing a peak at 4300 nm from the range of data points produced.

21. The method of claim 17, wherein the infrared light comprises wavelengths in the mid-infrared range and the near-infrared range.

22. The method of claim 17, wherein analyzing the downhole fluid sample is performed by infrared spectroscopy.

23. A downhole tool apparatus for detecting carbon dioxide and hydrogen sulfide, comprising:

a tool body comprising a probe, a pump, and an analyzer;

wherein the probe is adapted to pull a downhole fluid sample from a formation in a well;

wherein the analyzer comprises an infrared light source and a detector; and wherein the analyzer analyzes the downhole fluid sample by illuminating the downhole fluid sample by light emitting from the infrared light source of sufficient wavelength to detect carbon dioxide and hydrogen sulfide, detects light that interacts with the downhole fluid sample, measures the detected light to produce a range of data points that indicate the amount of carbon dioxide and hydrogen sulfide present in the downhole fluid sample, and determines any $H_2O$ content in the downhole fluid sample and compensates for any wavelength shift in the detected light and resulting data points effected by the $H_2O$ content;

wherein the infrared light source emits infrared light having wavelengths of 1900 nm or greater.

24. The downhole tool apparatus of claim 23, wherein the infrared light source emits light having wavelengths of from 2500 to 5000 nm.

25. The downhole tool apparatus of claim 23, wherein the infrared light source emits light having wavelengths of from 4000 to 4500 nm.

26. The downhole tool apparatus of claim 23, wherein the analyzer is capable of operating in a downhole environment.

27. The downhole tool apparatus of claim 23, wherein the pump pulls the formation fluid sample from the formation to inside the downhole tool in order to analyze the downhole fluid.

\* \* \* \* \*